US011650277B2

United States Patent
Wenger et al.

(10) Patent No.: US 11,650,277 B2
(45) Date of Patent: May 16, 2023

(54) TTFIELD TREATMENT WITH OPTIMIZATION OF ELECTRODE POSITIONS BASED ON LOW FREQUENCY (<1MHZ) AC CONDUCTIVITY ESTIMATES DERIVED FROM TWO MRI IMAGES HAVING DIFFERENT REPETITION TIMES

(71) Applicant: Novocure Limited, St. Helier (JE)

(72) Inventors: Cornelia Wenger, Ericeira (PT); Catherine Tempel-Brami, Matan (IL); Hadas Sara Hershkovich, Kiryat Motzkin (IL); Moshe Giladi, Moshav Herut (IL); Zeev Bomzon, Kiryat Tivon (IL)

(73) Assignee: Novocure GmbH, Root (CH)

( * ) Notice: Subject to any disclaimer, the term of this patent is extended or adjusted under 35 U.S.C. 154(b) by 240 days.

(21) Appl. No.: 16/378,826

(22) Filed: Apr. 9, 2019

(65) Prior Publication Data

US 2019/0308016 A1 Oct. 10, 2019

Related U.S. Application Data

(60) Provisional application No. 62/655,670, filed on Apr. 10, 2018.

(51) Int. Cl.
*G01R 33/56* (2006.01)
*A61N 1/36* (2006.01)
(Continued)

(52) U.S. Cl.
CPC ............ *G01R 33/56* (2013.01); *A61B 5/0042* (2013.01); *A61B 5/053* (2013.01); *A61B 5/055* (2013.01);
(Continued)

(58) Field of Classification Search
CPC ............... G01R 33/56; G01R 33/4808; G01R 33/5602; G01R 33/5607; G01R 33/5608;
(Continued)

(56) References Cited

U.S. PATENT DOCUMENTS 6,868,289 B2 3/2005 Palti
7,016,725 B2 3/2006 Palti
(Continued)

OTHER PUBLICATIONS

Herreros, Q., "Very low field magnetic resonance imaging," HAL Archive, 2014. p. 1-159 (Year: 2014).*
(Continued)

*Primary Examiner* — Keith M Raymond
*Assistant Examiner* — Sean A Frith
(74) *Attorney, Agent, or Firm* — Potomac Law Group, PLLC

(57) ABSTRACT

A 3D model of AC electrical conductivity (at a given frequency) of an anatomic volume can be created by obtaining two MRI images of the anatomic volume, where the two images have different repetition times. Then, for each voxel in the anatomic volume, a ratio IR of the intensity of the corresponding voxels in the two MRI images is calculated. This calculated IR is then mapped into a corresponding voxel of a 3D model of AC electrical conductivity at the given frequency. The given frequency is below 1 MHz (e.g., 200 kHz). In some embodiments, the 3D model of AC electrical conductivity at the given frequency is used to determine the positions for the electrodes in TTFields (Tumor Treating Fields) treatment.

19 Claims, 2 Drawing Sheets

(51) Int. Cl.
*A61B 5/00* (2006.01)
*A61N 1/04* (2006.01)
*A61B 5/055* (2006.01)
*A61B 5/053* (2021.01)
*G01R 33/48* (2006.01)
*A61N 1/00* (2006.01)
*G01R 33/58* (2006.01)

(52) U.S. Cl.
CPC ............. *A61N 1/00* (2013.01); *A61N 1/0476* (2013.01); *A61N 1/36002* (2017.08); *G01R 33/4808* (2013.01); *G01R 33/5602* (2013.01); *G01R 33/5607* (2013.01); *G01R 33/5608* (2013.01); *A61B 2576/026* (2013.01); *G01R 33/58* (2013.01)

(58) Field of Classification Search
CPC ....... G01R 33/58; A61B 5/0042; A61B 5/053; A61B 5/055; A61B 2576/026; A61N 1/00; A61N 1/0476
See application file for complete search history.

(56) References Cited

U.S. PATENT DOCUMENTS

| | | | |
|---|---|---|---|
| 7,089,054 B2 | 8/2006 | Palti | |
| 7,136,699 B2 | 11/2006 | Palti | |
| 7,146,210 B2 | 12/2006 | Palti | |
| 7,333,852 B2 | 2/2008 | Palti | |
| 7,467,011 B2 | 12/2008 | Palti | |
| 7,519,420 B2 | 4/2009 | Palti | |
| 7,565,205 B2 | 7/2009 | Palti | |
| 7,565,206 B2 | 7/2009 | Palti | |
| 7,599,745 B2 | 10/2009 | Palti | |
| 7,599,746 B2 | 10/2009 | Palti | |
| 7,706,890 B2 | 4/2010 | Palti | |
| 7,715,921 B2 | 5/2010 | Palti | |
| 7,805,201 B2 | 9/2010 | Palti | |
| 7,890,183 B2 | 2/2011 | Palti et al. | |
| 7,912,540 B2 | 3/2011 | Palti | |
| 7,917,227 B2 | 3/2011 | Palti | |
| 8,019,414 B2 | 9/2011 | Palti | |
| 8,027,738 B2 | 9/2011 | Palti | |
| 8,170,684 B2 | 5/2012 | Palti | |
| 8,175,698 B2 | 5/2012 | Palti et al. | |
| 8,229,555 B2 | 7/2012 | Palti | |
| RE43,618 E | 8/2012 | Palti | |
| 8,244,345 B2 | 8/2012 | Palti | |
| 8,406,870 B2 | 3/2013 | Palti | |
| 8,447,395 B2 | 5/2013 | Palti et al. | |
| 8,447,396 B2 | 5/2013 | Palti et al. | |
| 8,465,533 B2 | 6/2013 | Palti | |
| 8,706,261 B2 | 4/2014 | Palti | |
| 8,715,203 B2 | 5/2014 | Palti | |
| 8,718,756 B2 | 5/2014 | Palti | |
| 8,764,675 B2 | 7/2014 | Palti | |
| 9,023,090 B2 | 5/2015 | Palti | |
| 9,023,091 B2 | 5/2015 | Palti | |
| 9,039,674 B2 | 5/2015 | Palti et al. | |
| 9,056,203 B2 | 6/2015 | Palti et al. | |
| 9,307,925 B2 | 4/2016 | Russell et al. | |
| 9,440,068 B2 | 9/2016 | Palti et al. | |
| 9,655,669 B2 | 5/2017 | Palti et al. | |
| 9,750,934 B2 | 9/2017 | Palti et al. | |
| 9,910,453 B2 | 3/2018 | Wasserman et al. | |
| 10,188,851 B2 | 1/2019 | Wenger et al. | |
| 10,441,776 B2 | 10/2019 | Kirson et al. | |
| 2013/0109996 A1* | 5/2013 | Turnbull | A61B 5/7264 600/544 |
| 2016/0055304 A1* | 2/2016 | Russell | A61N 1/36034 705/3 |
| 2016/0081577 A1* | 3/2016 | Sridhar | A61B 5/742 600/383 |
| 2017/0120041 A1 | 5/2017 | Wenger et al. | |
| 2017/0185740 A1* | 6/2017 | Seegerer | A61B 6/5235 |
| 2017/0215939 A1 | 8/2017 | Palti et al. | |
| 2017/0281934 A1 | 10/2017 | Giladi et al. | |
| 2018/0001075 A1 | 1/2018 | Kirson et al. | |
| 2018/0008708 A1 | 1/2018 | Giladi et al. | |
| 2018/0050200 A1 | 2/2018 | Wasserman et al. | |
| 2018/0160933 A1 | 6/2018 | Urman et al. | |
| 2018/0202991 A1 | 7/2018 | Giladi et al. | |
| 2019/0117956 A1 | 4/2019 | Wenger et al. | |
| 2019/0298982 A1 | 10/2019 | Story et al. | |
| 2019/0307781 A1 | 10/2019 | Krex et al. | |
| 2019/0308016 A1 | 10/2019 | Wenger et al. | |

OTHER PUBLICATIONS

International Search Report and Written Opinion issued for application No. PCT/IB2019/052931 dated Jul. 23, 2019.
Michel et al., "Electrical conductivity and permittivity maps of brain tissues derived from water content based on T1-weighted acquistions," Magnetic Resonance in Medicine, vol. 77, Issue 3, pp. 1094-1103, Mar. 2017.
Sarracanie et al., "Low-Cost High-Performance MRI," Scientific Reports, vol. 5, No. 1, pp. 1-3, Oct. 2015.
European Search Report issued in application No. EP21150622 dated May 7, 2021.
Wenger et al., "Mapping the Brain's water content and low-frequency electrical properties through T1-weighted imaging," Proceedings of the International Society for Magnetic Resonance in Medicine, Jun. 16-21, 2018, No. 5104.
Collins et al., "Calculation of Radiofrequency Electromagnetic Fields and Their Effects in MRI of Human Subjects," Magnetic Resonance in Medicine, vol. 65, pp. 1470-1482, Mar. 2011.
Duan et al., "Boosting magnetic resonance imaging signal-to-noise ratio using magnetic metamaterials," Communications Physics, p. 235, 2019.

* cited by examiner

TTFIELD TREATMENT WITH OPTIMIZATION OF ELECTRODE POSITIONS BASED ON LOW FREQUENCY (<1MHZ) AC CONDUCTIVITY ESTIMATES DERIVED FROM TWO MRI IMAGES HAVING DIFFERENT REPETITION TIMES

CROSS REFERENCE TO RELATED APPLICATIONS

This application claims the benefit of U.S. Provisional Application 62/655,670 (filed Apr. 10, 2018), which is incorporated herein by reference in its entirety.

BACKGROUND

Tumor Treating Fields, or TTFields, are low intensity (e.g., 1-3 V/cm) alternating electric fields within the intermediate frequency range (100-300 kHz). This non-invasive treatment targets solid tumors and is described in U.S. Pat. No. 7,565,205, which is incorporated herein by reference in its entirety. TTFields are approved for the treatment of glioblastoma multiforme, and may be delivered, for example, via the Optune™ system comprising transducer arrays placed on the patient's shaved head. TTFields are typically delivered through two pairs of transducer arrays that generate perpendicular fields within the treated tumor. More specifically, for the Optune system one pair of electrodes is located to the left and right (LR) of the tumor, and the other pair of electrodes is located anterior and posterior (AP) to the tumor.

In-vivo and in-vitro studies show that the efficacy of TTFields therapy increases as the intensity of the electric field increases. Therefore, optimizing array placement on the patient's scalp to increase the intensity in the diseased region of the brain is standard practice for the Optune system. For improved treatment, the transducers' position may be adapted according to patient-specific head anatomy and tumor location. The transducers' position, as well as the electrical properties (EPs) of brain tissues, may be used to determine how TTFields distribute within the head. Array placement optimization may be done using a variety of conventional approaches such as placing the arrays on the scalp as close to the tumor as possible, using the NovoTal™ system, or using the approach described in U.S. Pat. No. 10,188,851, which is incorporated herein by reference in its entirety.

U.S. Pat. No. 10,188,851 explains that the position of the electrodes can be optimized by obtaining electrical conductivity measurements in an anatomic volume based on MRIs using diffusion weighted imaging (DWI) or diffusion tensor imaging (DTI), and subsequently generating a 3D map of the conductivity of the brain directly from the obtained electrical conductivity or resistivity measurements, without segmenting the anatomic volume into tissue types. While this approach has a number of advantages, it is relatively slow and typically provides images with a relatively low number of slices.

SUMMARY OF THE INVENTION

One aspect of the invention is directed to a first method of creating a 3D model of AC electrical conductivity or resistivity of an anatomic volume at a given frequency below 1 MHz. The first method comprises obtaining first and second MRI images of the anatomic volume, with associated first and second repetition times, respectively. The first and second repetition times are different. For each voxel in the anatomic volume, a ratio IR of an intensity of a corresponding voxel in the first MRI image to an intensity of a corresponding voxel in the second MRI image is calculated. The calculated IR for each voxel in the anatomic volume is then mapped into a corresponding voxel of a 3D model of AC electrical conductivity or resistivity at the given frequency.

In some instances of the first method, the given frequency is between 100 and 300 kHz. In some instances of the first method, the given frequency is between 180 and 220 kHz. In some instances of the first method, the first MRI image is a T1 image and the second MRI image is a T1 image. In some instances of the first method, the first MRI image is a T1 image and the second MRI image is a proton density image. In some instances of the first method, the first repetition time is between 400 and 800 ms and the second repetition time is between 2 and 5 seconds.

In some instances of the first method, the anatomic volume comprises white matter and grey matter of a brain. In some instances of the first method, the 3D model of AC electrical conductivity or resistivity is a 3D model of AC electrical conductivity.

Another aspect of the invention is directed to a second method of optimizing positions of a plurality of electrodes placed on a subject's body, where the electrodes are used to impose an electric field in target tissue within an anatomic volume at a given frequency below 1 MHz. The second method comprises obtaining first and second MRI images of the anatomic volume, with associated first and second repetition times, respectively. The first and second repetition times are different. For each voxel in the anatomic volume, a ratio IR of an intensity of a corresponding voxel in the first MRI image to an intensity of a corresponding voxel in the second MRI image is calculated. The calculated IR for each voxel in the anatomic volume is then mapped into a corresponding voxel of a 3D model of AC electrical conductivity or resistivity at the given frequency. The second method also comprises identifying a location of the target tissue within the anatomic volume; and determining positions for the electrodes based on the 3D model of electrical conductivity or resistivity and the location of the target tissue.

In some instances of the second method, the given frequency is between 100 and 300 kHz. In some instances of the second method, the given frequency is between 180 and 220 kHz. In some instances of the second method, the first MRI image is a T1 image and the second MRI image is a T1 image. In some instances of the second method, the first MRI image is a T1 image and the second MRI image is a proton density image. In some instances of the second method, the first repetition time is between 400 and 800 ms and the second repetition time is between 2 and 5 seconds.

Some instances of the second method further comprise affixing the electrodes to the subject's body at the determined positions and applying electrical signals between the affixed electrodes, so as to impose the electric field in the target tissue.

In some instances of the second method, the anatomic volume comprises white matter and grey matter of a brain. In some instances of the second method, the anatomic volume is a brain, and the determination of positions for the electrodes is based on a composite model in which the 3D model of electrical conductivity or resistivity of the brain is surrounded by a model of at least one shell having a constant conductivity.

In some instances of the second method, the anatomic volume is a brain surrounded by cerebrospinal fluid, and the determination of positions for the electrodes is based on a composite model in which the 3D model of electrical conductivity or resistivity of the brain is surrounded by a model of at least one shell having a constant conductivity.

In some instances of the second method, the 3D model of electrical conductivity or resistivity is a 3D model of electrical conductivity.

DESCRIPTION OF THE PREFERRED EMBODIMENTS

This application describes an approach for creating realistic head models for simulating TTFields that is much more computationally efficient and provides higher resolution than the prior art approach described in U.S. Pat. No. 10,188,851. More specifically, instead of determining the conductivity for each voxel in an anatomic volume based on DWI or DTI, the conductivity for each voxel is determined based on two MRI images with different repetition times. (For example, a first set of T1 MRI images captured with a repetition time of 700 ms and a second set of T1 MRI images captured with a repetition time of 4 seconds.)

Using the image ratio between two MRI images instead of DWI or DTI images (as in the '851 patent) provides improved results because the number of frames required to form a single DTI image slice is much higher than the number of frames required to form a single T1 image slice. As a result, DTI images will include far fewer slices than T1 images (assuming the patient spends the same amount of time spent in the MRI machine).

This description is divided into two parts: Part 1 provides a detailed description of methods for creating realistic head models for TTFields simulations from MRI data with minimal user intervention. Part 2 provides a detailed description on how to optimize TTFields array positions using the model created in part 1.

Figure 1:
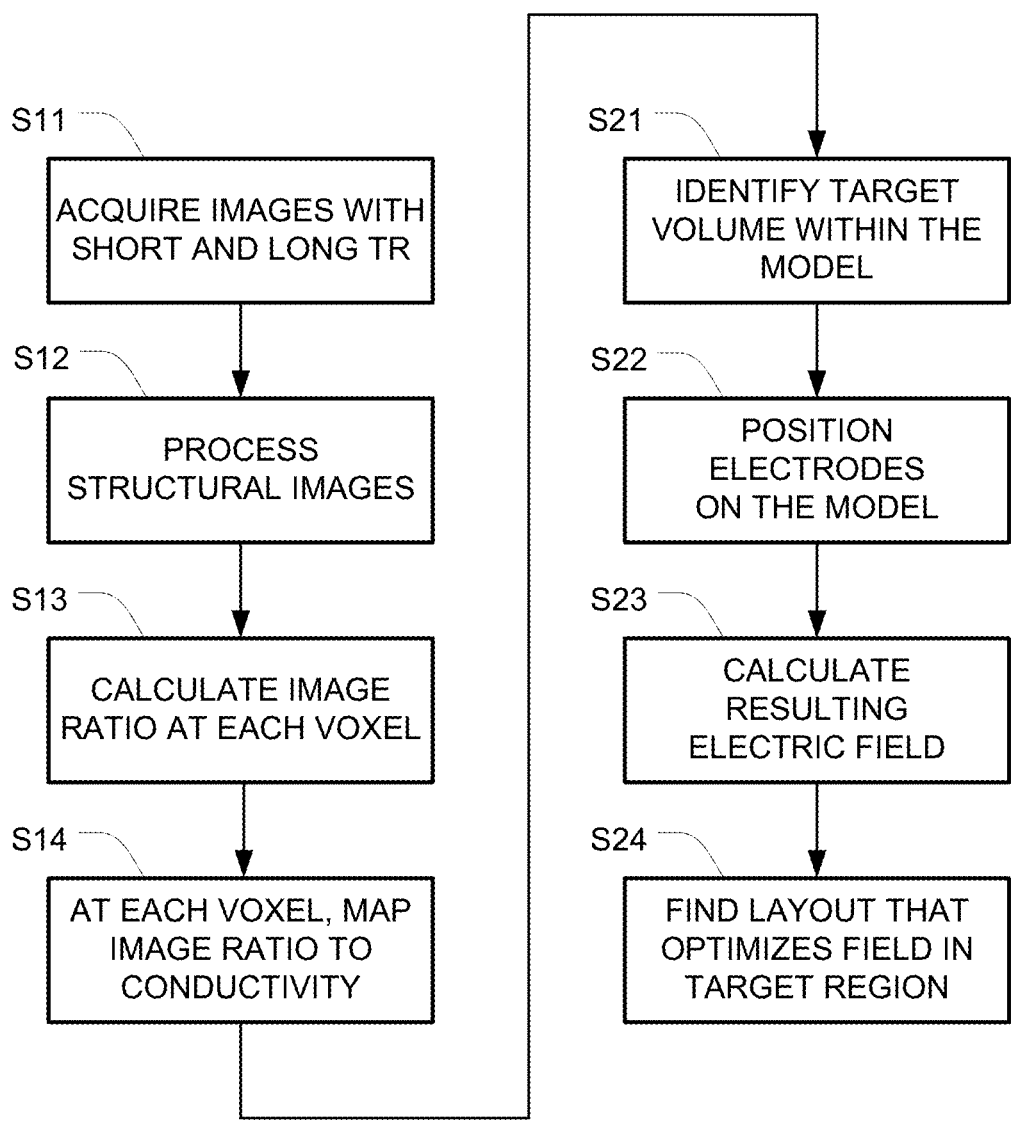
FIG. 1 is a flowchart of one example for creating a model of a head and optimizing the electric field using that model.

FIG. 1 is a flowchart of one example for creating the model (in steps S11-S14) and optimizing the electric field using that model (steps S21-S24).

Part 1: Creation of a realistic computational phantom from MRI data.

Creating an accurate computational phantom involves accurately mapping the electric properties (e.g., conductivity, resistivity) at each point within the computational phantom.

Mapping the electric properties directly using MRI sequences reduces the need for accurate tissue segmentation (which is a time-consuming and labor-intensive task) because the electric properties of every point are defined directly from the MRI, and not from the tissue type to which they are assigned to during the segmentation. Therefore, the segmentation process can be simplified or even eliminated without compromising the accuracy of the computational phantom. Note that while the embodiments described herein discuss mapping conductivity, alternative embodiments can provide similar results by mapping a different electrical property such as resistivity.

Steps S11-S14 in FIG. 1 depict one example of a set of steps that may be used to generate a computational phantom representing a patient based on MRI conductivity measurements.

Step S11 is the image acquisition step. In this step, both structural data and data from which conductivity maps can be calculated are acquired. Structural data can be obtained for instance from standard $T_1$ and $T_2$ MRI sequences. As explained below, the conductivity maps are generated from two MRI sequences having different repetition times. Therefore, the image acquisition step S11 must include acquisition of first and second MRI images of the anatomic volume at issue with different repetition times. In one example, the first MRI image of the anatomic volume could be a T1 image with a repetition time of 700 ms, and the second MRI image of the anatomic volume could be a T1 image with a repetition time of 4 seconds. In another example, the first MRI image of the anatomic volume could be a T1 image with a repetition time of 700 ms, and the second MRI image of the anatomic volume could be a standard proton density (PD) image with a repetition time between 2 and 3 seconds.

In order to create a good computational phantom, high resolution images should be obtained. A resolution of at least 1 mm×1 mm×1 mm for both structural and conductivity-related images is preferable. Lower resolution images may be used for one or both of these types of images, but the lower resolution will yield less accurate phantoms.

Optionally, the data set may be inspected and images affected by large artifacts may be removed. Scanner-specific pre-processing may be applied. For example, images may be converted from DICOM format to NIFTI. A different step of preprocessing may be to register all images to a standard space (for example the Montreal Neurological Institute, MNI, space). This can be done using readily available software packages including but not limited to FSL FLIRT, and SPM.

Step S12 is the step of processing structural images. As mentioned above, the work-flow presented here utilizes MRI-based conductivity measurements to create the computational phantom. However, structural images may still be used to identify the boundaries of the head, as well as identify regions belonging to specific tissues within the brain in which it might be advantageous to assign typical conductivity values that are not derived from the MRI measurements. For example, because the water content is relatively low in the skull and scalp, the approach described herein is not accurate for determining the conductivity within those regions. To avoid this shortcoming, it may be advantageous to manually or automatically identify and segment the skull and scalp within the images, and assign typical conductivity values to the regions corresponding to these layers (but still rely on the MRI-based measurements for the regions corresponding to the brain, as described below).

For example, shells or convex hulls of the outer tissues could be used as a model of the skull and the scalp. If a rough segmentation of the outer layers is available, the creation of the corresponding convex hull is trivial and can be performed using standard algorithms and software. Another option is for the user to measure the thickness of the outer layers at a representative region (a region where the transducer arrays might be placed) through examination of the structural image. These measurements can be used to create concentric shells or layers which represent the skull and scalp. These layers might be obtained by deforming a default oval structure, which could be a default convex hull of a scalp segmentation.

Water content-based EP tomography (wEPT) is a method that utilizes the ratio of two T1-weighted images with different repetition times (TRs) to map electrical properties (EPs) based on empirically derived relationships between $T_1$ relaxation value (T1), water content (WC), and EPs. wEPT has been applied to map EPs of a healthy brain at 128 MHz using typical WC and EP values of healthy tissues reported in the literature to derive the empirical models. See E. Michel, D. Hernandez, and S. Y. Lee, "Electrical conductivity and permittivity maps of brain tissues derived from water content based on $T_1$-weighted acquisition," Magn. Reson. Med., vol. 77, pp. 1094-1103, 2016, which is incorporated by reference herein in its entirety. Michel explains that as one moves "closer to the ultra-high frequency (UHF) range, the EPs [of tissue] are almost entirely determined by the water content"; and at these frequencies (e.g., the 128 MHz frequency tested in Michel), the following equation:

$$WC = w_1 e^{-w_2 IR} \quad \text{(equation "1")},$$

can be used to determine water content from the image ratio (IR) of two T1-weighted MRI images with different TRs; and that the following equation $$\sigma = c_1 + c_2 e^{c_3 WC} \quad \text{(equation "2")}.$$

can be used to determine conductivity from water content.

Surprisingly the inventors have experimentally determined that even at frequencies of 200 kHz (which is over 500× lower than the 128 MHz frequency disclosed in Michel), equation 2 still provides a workable approximation for conductivity that is good enough for subsequent use in simulating the strength of TTFields in brain tissue. Two of the inventors' experiments are described immediately below.

In one experiment, 32 tissue samples from three different healthy calf brains and cerebrospinal fluid (CSF) samples of two pigs were analyzed. The image ratios of two T1-weighted MRI images with different TRs were calculated and the EPs of the samples were measured by connecting Ag\AgCl electrodes of an impedance meter to each sample and measuring the samples' dielectric properties utilizing the parallel plates method. The water content of the samples was estimated by measuring the difference between the samples' wet and dry weight.

Curve fitting with these measured values yields empirical models connecting IR to WC (coefficients of equation "1") and WC to an estimate of conductivity (coefficients of equation "2") for 200 kHz and 1 MHz. The optimal choice for the combination of TRs of the two T1-weighted images was estimated to be TRshort=700 ms and TRlong=4000 ms.

In another experiment, the applicability of equation 2 at 200 kHz was investigated using 4 rat brain tumor models. Imaging was performed in a Bruker IT icon scanner. For each rat, 3D in vivo images (including a T1 MRI sequence with a short repetition time, a T1 MRI sequence with a long repetition time, and a $T_2$ MRI sequence for segmentation of samples) with a total of 20 slices are acquired prior to euthanizing the animal. Then, curve fitting was used to map WC and conductivity at 200 kHz and 1 MHz. Usable maps of conductivity approximations at 200 kHz and conductivity approximations at 1 MHz were obtained.

Subsequently, a total of 35 excised samples were investigated by measuring the water content in the electrical properties of each of the samples. For each sample, measured values were compared to the median WC and EPs in the corresponding voxels of the conductivity map generated from the MRIs according to the segmentation performed on the $T_2$ image. For comparison of these in vivo MRI-based conductivity estimates, the model coefficients were adapted to account for the difference of measured T1, and EP values at lower ex vivo temperatures.

The experimental measurements revealed an average error for MRI-based water content estimates of 3.1% in both models. The experimental measurements also revealed an average error for the MRI-based conductivity estimates of 22.8% and 24.3% at 200 kHz (for two different models, respectively) and 26.4% and 23.9% at 1 MHz (for two different models, respectively). Measurement errors are estimated to be ~1% for WC and ~10% for the MRI-based conductivity estimates. And this level of accuracy in the conductivity estimates is adequate for running the TTFields simulations described in part 2 below.

Figure 2A:
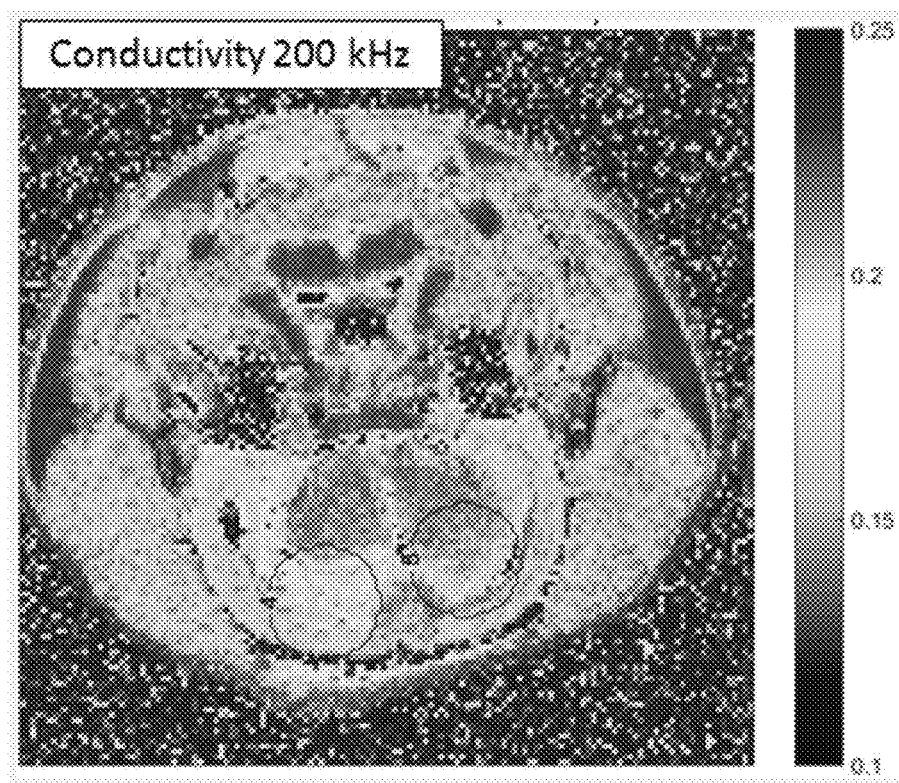
FIGS. 2A and 2B are in vivo conductivity estimate map at frequencies of 200 kHz and 1 MHz, respectively.
Figure 2B:
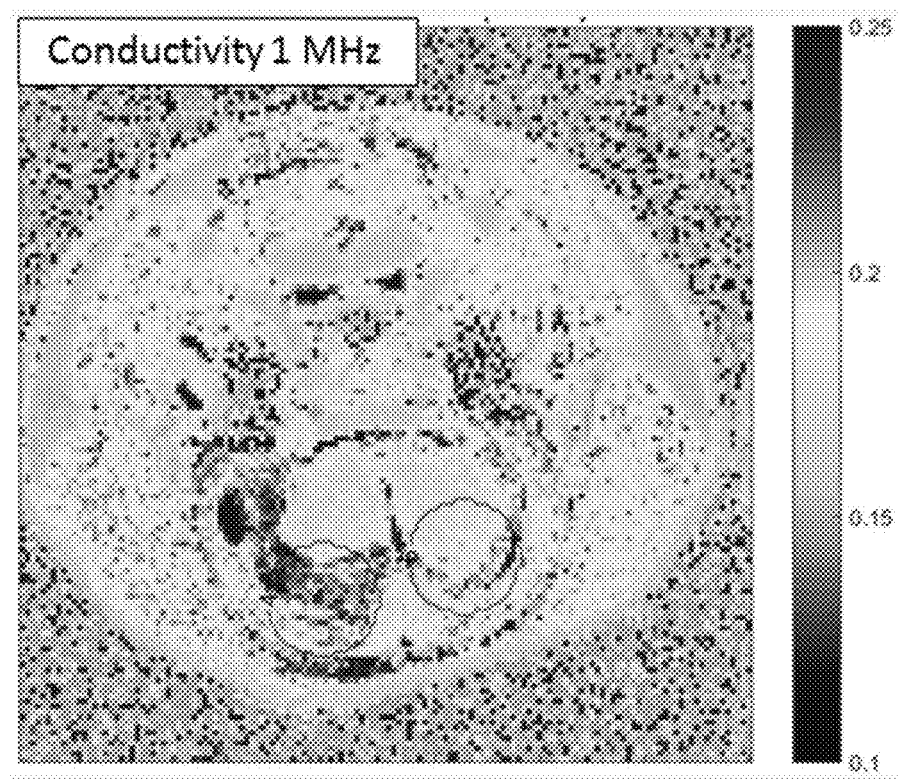

Anatomical structures and the tumor were clearly visible in the resulting conductivity estimate maps. See, for example, the in vivo 200 kHz conductivity estimate map and the 1 MHz conductivity estimate map depicted in FIG. 2A and FIG. 2B, respectively.

In view of these experimental results indicating that a 3D map of electrical conductivity at low frequencies (e.g., 200 kHz) of an anatomic volume can be generated directly from MRI data, it becomes possible to generate a 3D map of electrical conductivity of an individual person's head from MRI data without segmenting the MRI into tissue types, and to subsequently use that 3D map of electrical conductivity to optimize the position of the electrodes that are used to apply 200 kHz TTFields to a person's head (by running simulations using the 3D map, as described below in part 2).

Returning to FIG. 1, steps S13 and S14 collectively create a 3D conductivity map from the MRI images with the short and long repetition times that were previously acquired in step S11. More specifically, in step S13, the ratio IR of the intensity of each voxel in the first MRI image to the intensity of the corresponding voxel in the second MRI image is calculated for each voxel in the anatomic volume. Then, in step S14. the calculated IR for each voxel in the anatomic volume is mapped into a corresponding voxel of a 3D map of electrical conductivity at the given frequency without segmenting the anatomic volume into tissue types.

For any given set of settings for a given MRI machine, the set of coefficients w1 and w2 for the equation 1 above that provides the best fit between image ratio IR and water content can be determined. In addition, for any given frequency at which TTFields will ultimately be used, a set of coefficients c1, c2, and c3 for the equation 2 above that provides the best fit between water content and an estimate of conductivity can be determined.

Because equation 1 above is used to compute WC from IR, and equation 2 above is used to compute an estimate of conductivity from WC, and because the coefficients w1, w2, c1, c2, and c3 can all be determined in advance based on the known settings of the MRI machine and the known frequency at which the TTFields will be applied, it becomes possible to generate a lookup table that maps the IR at any given pixel to an estimate of conductivity for that pixel. When such a lookup table is used, step S14 can be implemented simply by taking the image ratio calculated in S13, plugging it into the lookup table, and obtaining the conductivity estimate from the lookup table. Alternatively, the mapping in step S14 may be implemented mathematically by curve fitting using equations 1 and 2 above. Alternatively, the mapping in step S14 may be implemented mathematically using a different set of curve fitting equations (e.g., fitting to a polynomial function instead of the exponential function that appears in equation 1).

After the conductivity map of the anatomic volume is generated in step S14, the resulting conductivity map may be merged with the conductivities of the shells that surround the anatomic volume (described above in connection with step S12). For example, in the context of a brain, an initial conductivity map of the gray matter, the white matter, and any tumors contained therein would be generated in step S14. And to finalize the model of the head, constant conductivity shells that represent the CSF, skull, and scalp are added to the initial conductivity map. Alternatively, because the water content of the CSF is sufficiently high, the initial conductivity map generated in step S14 could cover the gray matter, the white matter, any tumors contained therein, and the CSF. In this situation, to finalize the model of the head, constant conductivity shells that represent the skull and scalp are added to the initial conductivity map of the brain and CSF.

Optionally, when the fractional anisotropy (or any other measure that can be derived from the conductivity data) is found, then the neighboring elements are preferably checked to avoid outliers (for example, to eliminate a GM point that was identified inside the WM).

Part 2: Optimization of TTFields Array Positions Using Realistic Head Models

Optimization of array layouts means finding the array layout that optimizes the electric field within the diseased regions of the patient's brain (tumor). This optimization may be implemented by performing the following four steps: (S21) identifying the volume targeted for treatment (target volume) within the realistic head model; (S22) automatically placing transducer arrays and setting boundary conditions on the realistic head model; (S23) calculating the electric field that develops within the realistic head model once arrays have been placed on the realistic head model and boundary conditions applied; and (S24) running an optimization algorithm to find the layout that yields optimal electric field distributions within the target volume. A detailed example for implementing these four steps is provided below.

Step S21 involves locating the target volume within the realistic head model (i.e., defining a region of interest). A first step in finding a layout that yields optimal electric field distributions within the patient's body is to correctly identify the location and target volume, in which the electric field should be optimized.

In some embodiments, the target volume will be either the Gross Tumor Volume (GTV) or the Clinical Target Volume (CTV). The GTV is the gross demonstrable extent and location of the tumor, whereas the CTV includes the demonstrated tumors if present and any other tissue with presumed tumor. In many cases the CTV is found by defining a volume that encompasses the GTV and adding a margin with a predefined width around the GTV.

In order to identify the GTV or the CTV, it is necessary to identify the volume of the tumor within the MRI images. This can be performed either manually by the user, automatically, or using a semi-automatic approach in which user-assisted algorithms are used. When performing this task manually, the MRI data could be presented to a user, and the user could be asked to outline the volume of the CTV on the data. The data presented to the user could be structural MRI data (e.g., $T_1$, $T_2$ data). The different MRI modalities could be registered onto each other, and the user could be presented with the option to view any of the datasets, and outline the CTV. The user could be asked to outline the CTV on a 3D volumetric representation of the MRIs, or the user could be given the option of viewing individual 2D slices of the data, and marking the CTV boundary on each slice. Once the boundaries have been marked on each slice, the CTV within the anatomic volume (and hence within the realistic model) can be found. In this case, the volume marked by the user would correspond to the GTV. In some embodiments, the CTV could then be found by adding margins of a predefined width to the GTV. Similarly, in other embodiments, the user might be asked to mark the CTV using a similar procedure.

An alternative to the manual approach is to use automatic segmentation algorithms to find the CTV. These algorithms perform automatic segmentation algorithms to identify the CTV using the structural MRI data.

Optionally, semi-automatic segmentation approaches of the MRI data may be implemented. In an example of these approaches, a user iteratively provides input into the algorithm (e.g., the location of the tumor on the images, roughly marking the boundaries of the tumor, demarcating a region of interest in which the tumor is located), which is then used by a segmentation algorithm. The user may then be given the option to refine the segmentation to gain a better estimation of the CTV location and volume within the head.

Whether using automatic or semi-automatic approaches, the identified tumor volume would correspond with the GTV, and the CTV could then be found automatically by expanding the GTV volume by a pre-defined amount (e.g., defining the CTV as a volume that encompasses a 20 mm wide margin around the tumor).

Note that in some cases, it might be sufficient for the user to define a region of interest in which they want to optimize the electric field. This region of interest might be for instance a box volume, a spherical volume, or volume of arbitrary shape in the anatomic volume that encompasses the tumor. When this approach is used, complex algorithms for accurately identifying the tumor may not be needed.

Step S22 involves automatically calculating the position and orientation of the arrays on the realistic head model for a given iteration. Each transducer array used for the delivery of TTFields in the Optune™ device comprise a set of ceramic disk electrodes, which are coupled to the patient's head through a layer of medical gel. When placing arrays on real patients, the disks naturally align parallel to the skin, and good electrical contact between the arrays and the skin occurs because the medical gel deforms to match the body's contours. However, virtual models are made of rigidly defined geometries. Therefore, placing the arrays on the model requires an accurate method for finding the orientation and contour of the model surface at the positions where the arrays are to be placed, as well as finding the thickness/geometry of the gel that is necessary to ensure good contact of the model arrays with the realistic patient model. In order to enable fully automated optimization of field distributions these calculations have to be performed automatically.

A variety of algorithms to perform this task may be used, and one such algorithm is described in U.S. Pat. No. 10,188,851, which is incorporated herein by reference in its entirety.

Step S23 involves calculating the electric field distribution within the head model for the given iteration. Once the head phantom is constructed and the transducer arrays (i.e., the electrode arrays) that will be used to apply the fields are placed on the realistic head model, then a volume mesh, suitable for finite element (FE) method analysis, can be created. Next boundary conditions can be applied to the model. Examples of boundary conditions that might be used include Dirichlet boundary (constant voltage) conditions on the transducer arrays, Neumann boundary conditions on the transducer arrays (constant current), or floating potential boundary condition that set the potential at that boundary so that the integral of the normal component of the current density is equal to a specified amplitude. The model can then be solved with a suitable finite element solver (e.g., a low frequency quasistatic electromagnetic solver) or alternatively with finite difference (FD) algorithms. The meshing, imposing of boundary conditions and solving of the model can be performed with existing software packages such as Sim4Life, Comsol Multiphysics, Ansys, or Matlab. Alternatively, custom computer code that realizes the FE (or FD) algorithms could be written. This code could utilize existing open-source software resources such as C-Gal (for creating meshes), or FREEFEM++(software written in C++ for rapid testing and finite element simulations). The final solution of the model will be a dataset that describes the electric field distribution or related quantities such as electric potential within the computational phantom for the given iteration.

Step S24 is the optimization step. An optimization algorithm is used to find the array layout that optimizes the electric field delivery to the diseased regions of the patient's brain (tumor) for both application directions (LR and AP, as mentioned above). The optimization algorithm will utilize the method for automatic array placement and the method for solving the electric field within the head model in a well-defined sequence in order to find the optimal array layout. The optimal layout will be the layout that maximizes or minimizes some target function of the electric field in the diseased regions of the brain, considering both directions at which the electric field is applied. This target function may be for instance the maximum intensity within the diseased region or the average intensity within the diseased region. It also possible to define other target functions.

There are a number of approaches that could be used to find the optimal array layouts for patients, three of which are described below. One optimization approach is an exhaustive search. In this approach the optimizer will include a bank with a finite number of array layouts that should be tested. The optimizer performs simulations of all array layouts in the bank (e.g., by repeating steps S22 and S23 for each layout), and picks the array layouts that yield the optimal field intensities in the tumor (the optimal layout is the layout in the bank that yields the highest (or lowest) value for the optimization target function, e.g., the electric field strength delivered to the tumor).

Another optimization approach is an iterative search. This approach covers the use of algorithm such as minimum-descent optimization methods and simplex search optimization. Using this approach, the algorithm iteratively tests different array layouts on the head and calculates the target function for electric field in the tumor for each layout. This approach therefore also involves repeating steps S22 and S23 for each layout. At each iteration, the algorithm automatically picks the configuration to test based on the results of the previous iteration. The algorithm is designed to converge so that it maximizes (or minimizes) the defined target function for the field in the tumor.

Yet another optimization approach is based on placing a dipole at the center of the tumor in the model. This approach differs from the other two approaches, as it does not rely on solving field intensity for different array layouts. Rather, the optimal position for the arrays is found by placing a dipole aligned with the direction of the expected field at the center of the tumor in the model, and solving the electromagnetic potential. The regions on the scalp where the electric potential (or possibly electric field) is maximal will be the positions where the arrays are placed. The logic of this method is that the dipole will generate an electric field that is maximal at the tumor center. By reciprocity, if we were able to generate the field/voltage on the scalp that the calculation yielded, then we would expect to obtain a field distribution that is maximal at the tumor center (where the dipole was placed). The closest we can practically get to this with our current system is to place the arrays in the regions where the potential induced by the dipole on the scalp is maximal.

Note that alternative optimization schemes can be used to find an array layout that optimizes the electric field within diseased regions of the brain. For example, algorithms that combine the various approaches mentioned above. As an example of how these approaches may be combined, consider an algorithm in combining the third approach discussed above (i.e., positioning the dipole at the center of the tumor in the model) with the second approach (i.e., the iterative search). With this combination, an array layout is initially found using the dipole at the center of the tumor approach. This array layout is used as input to an iterative search that finds the optimal layout.

Once the layout that optimizes the electric field within the diseased regions of the patient's brain has been determined (e.g., using any of the approaches explained herein), the electrodes are positioned in the determined positions. AC voltages are then applied to the electrodes (e.g., as described in U.S. Pat. No. 7,565,205, which is incorporated herein by reference) to treat the disease.

Note also that the concepts described herein are not limited to representations of the outer layers (scalp, skull, CSF) as convex hulls, and other methods may be used to roughly approximate the MRI data. Examples include simple geometric forms such as ellipsoids, spheres, oval shaped structure or also other methods for creating an envelope of the tissues. Additionally, the concepts described herein are not restricted to an approximation of the outer layers, i.e., the scalp, skull and CSF layers can also be obtained through conventional segmentation of MRIs.

Note also that instead of using the segmentation of the scalp, skull, and CSF, an approximation of these outer layers may be used. For example, the user may be asked to measure the thickness of the scalp, skull, and CSF in a representative region. These tissues are then approximated as concentric geometric entities (similar to a default convex hull of a scalp, a sphere, an ellipsoid, etc.) with the user-measured thicknesses surrounding the brain. This approximation simulates the head as an (almost) oval shaped structure, ignoring features such as the ears, nose, mouth and jaw. However, since the arrays and treatment are delivered only to the supratentorial region of the head, this approximation appears to be justified. In some embodiments it might also be possible to combine two or more of the three tissue types into one layer and assign a single conductivity value to that layer. For instance, the scalp and skull may be introduced as one layer with a single conductivity (and optionally a uniform thickness).

Computational phantoms built in this manner could also be used for other applications in which calculating electric field and or electric current distributions within the head may be useful. These applications include, but are not limited to: direct and alternating current trans-cranial stimulation; simulations of implanted stimulatory electrode field maps; planning placement of implanted stimulatory electrodes; and source localization in EEG.

Finally, although this application describes a method for optimizing array layouts on the head, it could potentially be extended for optimizing array layouts for treatment of other body regions such as the thorax or abdomen.

While the present invention has been disclosed with reference to certain embodiments, numerous modifications, alterations, and changes to the described embodiments are possible without departing from the sphere and scope of the present invention, as defined in the appended claims.

Accordingly, it is intended that the present invention not be limited to the described embodiments, but that it has the full scope defined by the language of the following claims, and equivalents thereof.

What is claimed is:

1. A method of creating a 3D model of AC electrical conductivity or resistivity of an anatomic volume at a given frequency, the method comprising the steps of:
    obtaining a first MRI image of the anatomic volume, the first MRI image having an associated first frequency and an associated first repetition time;
    obtaining a second MRI image of the anatomic volume, the second MRI image having an associated second frequency and an associated second repetition time that is different from the first repetition time;
    calculating, for each voxel in the anatomic volume, a ratio IR of an intensity of a corresponding voxel in the first MRI image to an intensity of a corresponding voxel in the second MRI image; and
    mapping the calculated IR for each voxel in the anatomic volume into a corresponding voxel of a 3D model of AC electrical conductivity or resistivity at the given frequency, wherein the given frequency is below 1 MHz, wherein the given frequency is different from the first frequency, and wherein the given frequency is different from the second frequency.

2. The method of claim 1, wherein the given frequency is between 100 and 300 kHz.

3. The method of claim 1, wherein the given frequency is between 180 and 220 kHz.

4. The method of claim 1, wherein the first MRI image is a T1 image and the second MRI image is a T1 image.

5. The method of claim 1, wherein the first MRI image is a T1 image and the second MRI image is a proton density image.

6. The method of claim 1, wherein the first repetition time is between 400 and 800 ms and the second repetition time is between 2 and 5 seconds.

7. The method of claim 1, wherein the anatomic volume comprises white matter and grey matter of a brain.

8. The method of claim 1, wherein the 3D model of AC electrical conductivity or resistivity is a 3D model of AC electrical conductivity.

9. A method of optimizing positions of a plurality of electrodes placed on a subject's body, wherein the electrodes are used to impose an electric field in target tissue within an anatomic volume at a given frequency, the method comprising the steps of:
    obtaining a first MRI image of the anatomic volume, the first MRI image having an associated first frequency and an associated first repetition time;
    obtaining a second MRI image of the anatomic volume, the second MRI image having an associated second frequency and an associated second repetition time that is different from the first repetition time;
    calculating, for each voxel in the anatomic volume, a ratio IR of an intensity of a corresponding voxel in the first MRI image to an intensity of a corresponding voxel in the second MRI image;
    mapping the calculated IR for each voxel in the anatomic volume into a corresponding voxel of a 3D model of electrical conductivity or resistivity at the given frequency, wherein the given frequency is below 1 MHz, wherein the given frequency is different from the first frequency, and wherein the given frequency is different from the second frequency;
    identifying a location of the target tissue within the anatomic volume; and
    determining positions for the electrodes based on the 3D model of electrical conductivity or resistivity at the given frequency generated in the mapping step and the location of the target tissue identified in the identifying step.

10. The method of claim 9, wherein the given frequency is between 100 and 300 kHz.

11. The method of claim 9, wherein the given frequency is between 180 and 220 kHz.

12. The method of claim 9, wherein the first MRI image is a T1 image and the second MRI image is a T1 image.

13. The method of claim 9, wherein the first MRI image is a T1 image and the second MRI image is a proton density image.

14. The method of claim 9, wherein the first repetition time is between 400 and 800 ms and the second repetition time is between 2 and 5 seconds.

15. The method of claim 9, further comprising the steps of:
    affixing the electrodes to the subject's body at the positions determined in the determining step; and
    applying electrical signals between the electrodes subsequent to the affixing step, so as to impose the electric field in the target tissue.

16. The method of claim 9, wherein the anatomic volume comprises white matter and grey matter of a brain.

17. The method of claim 9, wherein the anatomic volume is a brain, and
    wherein the determination of positions for the electrodes is based on a composite model in which the 3D model of electrical conductivity or resistivity of the brain is surrounded by a model of at least one shell having a constant conductivity.

18. The method of claim 9, wherein the anatomic volume is a brain surrounded by cerebrospinal fluid, and
    wherein the determination of positions for the electrodes is based on a composite model in which the 3D model of electrical conductivity or resistivity of the brain is surrounded by a model of at least one shell having a constant conductivity.

19. The method of claim 9, wherein the 3D model of electrical conductivity or resistivity is a 3D model of electrical conductivity.

* * * * *